(12) United States Patent
Mohn et al.

(10) Patent No.: US 9,082,273 B2
(45) Date of Patent: Jul. 14, 2015

(54) STIMULATION APPARATUS

(75) Inventors: Louise Mohn, Oslo (NO); Ole Brix, Bergen (NO); Bard Henriksen, Bergen (NO); Inge Klepsvik, Bergen (NO)

(73) Assignee: Louise Mohn, London (GB)

( * ) Notice: Subject to any disclaimer, the term of this patent is extended or adjusted under 35 U.S.C. 154(b) by 0 days.

(21) Appl. No.: 13/881,749

(22) PCT Filed: Oct. 28, 2011

(86) PCT No.: PCT/EP2011/069049
§ 371 (c)(1),
(2), (4) Date: Oct. 31, 2013

(87) PCT Pub. No.: WO2012/056026
PCT Pub. Date: May 3, 2012

(65) Prior Publication Data
US 2014/0052199 A1    Feb. 20, 2014

(30) Foreign Application Priority Data

Oct. 28, 2010 (EP) .................................. 10189306
Jan. 28, 2011 (GB) .................................. 1101498.2

(51) Int. Cl.
*A61N 1/00* (2006.01)
*G08B 5/22* (2006.01)
*A61F 7/02* (2006.01)
(Continued)

(52) U.S. Cl.
CPC ... *G08B 5/22* (2013.01); *A61F 7/00* (2013.01); *A61F 7/02* (2013.01); *A61N 1/0456* (2013.01); *A61N 1/0492* (2013.01); *A61N 1/36* (2013.01); *A61N 1/37235* (2013.01); *A61B 19/44* (2013.01); *A61B 2017/00084* (2013.01); *A61F 2007/0058* (2013.01); *A61F 2007/0075* (2013.01); *A61F 2007/0093* (2013.01); *A61F 2007/0096* (2013.01); *A61F 2007/0295* (2013.01); *A61N 1/36021* (2013.01)

(58) Field of Classification Search
CPC ..................... A61B 5/0022; A61M 2205/3523
USPC ............................................... 607/3; 600/372
See application file for complete search history.

(56) References Cited

U.S. PATENT DOCUMENTS 4,919,139 A * 4/1990 Brodard .......................... 607/59
5,092,344 A    3/1992 Lee
(Continued)

FOREIGN PATENT DOCUMENTS

| EP | 0165049 | 12/1985 |
| JP | 2007-313102 | 12/2007 |
| WO | WO 97/18854 | 5/1997 |
| WO | WO 2007/107831 | 9/2007 |

OTHER PUBLICATIONS

International Patent Application No. PCT/EP2011/069049, International Search Report dated Feb. 1, 2012, 4 pages.

*Primary Examiner* — Nichole F Lavert
(74) *Attorney, Agent, or Firm* — Morgan Lewis & Bockius LLP

(57) ABSTRACT

An apparatus (1) for applying stimulation to a body has a distributed control system comprising a first CPU (7) in a main unit (24), a second CPU (30) in a display and control unit (2) and a further CPU 5 in each of one or more interface cards (3, 4). The second CPU (30) is configured to control the operation of the first CPU (7), while the first CPU (7) is configured to control and coordinate the operation of the CPUs (5) in each interface card (3, 4).

16 Claims, 5 Drawing Sheets

(51) Int. Cl.
*A61N 1/04* (2006.01)
*A61N 1/372* (2006.01)
*A61B 19/00* (2006.01)
*A61B 17/00* (2006.01)
*A61F 7/00* (2006.01)
*A61N 1/36* (2006.01)

(56) References Cited

U.S. PATENT DOCUMENTS

2005/0256550 A1 11/2005 Gilkerson et al.
2008/0021520 A1 1/2008 Dietrich
2010/0228304 A1* 9/2010 Kriksunov et al. ............... 607/3

* cited by examiner

STIMULATION APPARATUS

CROSS-REFERENCE TO RELATED APPLICATION

This application is a U.S. National Phase Application under 35 U.S.C. 371 claiming priority to International Application No. PCT/EP2011/069049 filed Oct. 28, 2011, which claims priority to European Patent Application No. 10189306.3 filed Oct. 28, 2010 and also claims priority to Great Britain Application No. 1101498.2 filed Jan. 28, 2011, wherein the entire contents of each application are incorporated herein by reference in their entireties.

FIELD OF THE INVENTION

The present invention relates to a stimulation apparatus. Particular examples of the invention relate to an apparatus for applying electrical stimulation, heat therapy and/or thermostimulation to a human or animal body.

BACKGROUND OF THE INVENTION

For a variety of therapeutic applications, several treatment modalities are currently known in the art including electrical stimulation, heat therapy and thermostimulation.

Electrical stimulation involves the application of an electrical current to a single muscle or a group of muscles through one or more stimulation pads that are temporarily attached to the skin. The resulting muscle contraction can produce a variety of effects from strengthening injured muscles and reducing edema to relieving pain and promoting healing. The pads are usually quite small and typically powered with a battery. This results in the application of a small amount of power and a low treatment depth of the resulting electric field. The shallow depth of the electric field generated by conventional electrical stimulation systems limits performance and patient benefit. Some systems have attempted to address this limitation by applying more current, often from a line or mains supply source. However, the small size of conventional electrical stimulation pads is such that on the application of larger amounts of power, i.e. the use of higher currents, patients often report the experience of pain or discomfort.

Heat therapy itself is very useful as it has a number of effects such as relaxation of muscle spasm and increased blood flow that promotes healing. However, combination therapy, i.e. the synergistic use of other modalities such as massage, ultrasound and/or electrical stimulation has been found to be more effective than heat therapy alone.

Thermostimulation is one such combination therapy that involves the use of heat therapy and electrical stimulation simultaneously. With thermostimulation, the healing benefits of heat are provided along with the strengthening, toning, pain relieving and healing benefits of electrical stimulation. Moreover, the application of heat has been found effective in that it allows the patient to tolerate higher currents. This yields higher electric field strengths, greater depths of penetration and, therefore, more positive results than could be achieved with electrical stimulation without heat.

Many known electrical stimulation systems have two to four channels and therefore allow only one or two pads to be applied to a patient. The usefulness of such systems is limited by the small number of channels, which prevents electrical stimulation being applied to more than two regions of the body at once, and thereby prolongs the time taken for treatment if numerous regions of the body need to be treated. A further disadvantage of these known electrical stimulation systems is that all of the pads are controlled by a common controller, which generates electrical pulses for all of the pads and determines the amplitude and duration of each electrical pulse. A user has little or no control over the pulses that are generated and, indeed, it is often not possible for a user to know the properties of the pulses without using an oscilloscope. Yet another disadvantage of these known electrical stimulation systems is that they are limited in the number of treatment modalities that they can apply. For example, some systems can only apply electrical stimulation, whilst other systems can apply only thermostimulation.

An improved thermostimulation apparatus is disclosed by the Applicant's earlier patent application, International Patent Application No. PCT/GB10/002132, filed on 18 Nov. 2010 and entitled "Thermostimulation System Including Multilayer Pads with Integrated Temperature Regulation", the entire contents of which are incorporated herein by reference. This apparatus has a console for providing electrical currents for thermal and electrical stimulation in response to a first input from an operator via at least one electrical connector. An inline control system is coupled to the electrical connector for regulating the currents in response to a second input from an operator and a temperature feedback signal via a second electrical connector. A thermostimulation pad is coupled to the inline control system via the second electrical connector. A plurality of inline control systems and thermostimulation pads can be connected to the console and, in this case, each inline control system is independent of the other inline control systems. Thus, it is not possible to coordinate the times at which each thermostimulation pad generates an electrical pulse.

SUMMARY OF THE INVENTION

It is a preferred aim of the invention to overcome or mitigate the problems and disadvantages described above.

A first aspect of the invention provides an apparatus for applying stimulation to a body, the apparatus comprising a main device for connection to one or more interface devices, each interface device being operable to apply stimulation to the body and comprising a controller for controlling application of stimulation to the body, wherein the main device comprises a controller for controlling the operation of the controller of each interface device.

Preferably, any of the controllers described herein are programmable. For example, any of the controllers may be implemented by a microprocessor, microcontroller or some other form of central processing unit. As another example, any of the controllers may be implemented by programmable logic, such as a field-programmable gate array (FPGA). Alternatively, any of the controllers may be implemented using discrete logic or an application-specific integrated circuit (ASIC).

The controller of the main device is preferably operable to control the operation of the controller of each interface device by coordinating and/or synchronising the times at which a plurality of interface devices stimulate the body. The controller of the main device is preferably operable to generate a start signal which, when received by the controller of an interface device, causes the interface device to apply stimulation to the body. The controller of the main device is preferably operable to control the operation of the controller of each interface device by transmitting a respective message to the controller of an interface device, wherein the message specifies one or more parameters of stimulation to be applied to the body. The main device is preferably operable to communicate with a display device, and the controller of the main device is preferably operable to be controlled by the display device. The controller of the main device is preferably operable to receive a message from the display device, wherein the message specifies one or more parameters of stimulation to be applied to the body by one or more of the interface devices.

A further aspect of the invention provides an apparatus for applying stimulation to a body, the apparatus comprising an interface device operable to apply stimulation to the body and comprising a controller for controlling application of stimulation to the body, wherein the controller of the interface device is operable to be controlled by a controller of a main device when said interface device is connected to said main device. The controller of the interface device is preferably operable to cause the interface device to begin applying stimulation to the body when a start signal is received from the controller of the main device. The controller of the interface device is preferably operable to cause the interface device to apply stimulation to the body in accordance with one or more parameters specified in a message received from the controller of the main device.

A further aspect of the invention provides an apparatus for applying stimulation to a body, the apparatus comprising a display device operable to communicate with a main device, the main device comprising a controller and being suitable for connection to one or more interface devices, each interface device being operable to apply stimulation to the body under the control of the controller of the main device, wherein the display device comprises a controller that is programmed to control the operation of the controller of the main device. The controller of the display device is operable to control the operation of the controller of the main device by instructing the main device to transmit a start signal to one or more interface devices, wherein the start signal is operable to cause an interface device to apply stimulation to the body. The main device preferably comprises a computer program for allowing a user to design a stimulation program. The controller of the display device is preferably operable to transmit a message to the main device, wherein the message specifies one or more parameters of stimulation to be applied to the body by one or more of the interface devices. The parameters preferably include any one or more of: a total number of pulses in a sequence of pulses; an amplitude of one or more pulses; a time at which one or more pulses are to be generated; a number of times that a sequence of pulses is to be repeated; a temperature; and/or a length of time for which a temperature is to be generated.

A further aspect of the invention provides a processor-readable medium comprising instructions for execution by a processor of a main device for applying stimulation to a body, said main device being connectable to one or more interface devices, each interface device being operable to apply stimulation to the body and comprising a controller for controlling application of stimulation to the body, wherein the instructions are executable to cause the processor to control the operation of the controller of each interface device. The instructions are preferably executable to cause the processor of the main device to control the operation of the controller of each interface device by coordinating and/or synchronising the times at which a plurality of interface devices stimulate the body. The instructions are preferably executable to cause the processor to generate a start signal which, when received by the controller of an interface device, causes the interface device to apply stimulation to the body. The instructions are preferably executable to cause the processor to control the operation of the controller of each interface device by transmitting a respective message to the controller of an interface device, wherein the message specifies one or more parameters of stimulation to be applied to the body. The instructions are preferably executable to cause the processor to receive instructions and/or data from a display device, and to cause the processor to operate in accordance with the instructions and/or data received from the display device. The instructions are preferably executable to cause the processor to receive a message from the display device, wherein the message specifies one or more parameters of stimulation to be applied to the body by one or more of the interface devices.

A further aspect of the invention provides a processor-readable medium comprising instructions for execution by a processor of an interface device operable to apply stimulation to a body, said interface device being connectable to a main device, wherein the instructions are executable to cause the processor to receive instructions and/or data from the main device, and to cause the processor to operate in accordance with the instructions and/or data received from the main device. The instructions are preferably executable to cause the interface device to begin applying stimulation to the body when a start signal is received from the main device. The instructions are preferably executable to cause the interface device to apply stimulation to the body in accordance with one or more parameters specified in a message received from the main device.

A further aspect of the invention provides a processor-readable medium comprising instructions for execution by a processor, said processor being operable to communicate with a main device of an apparatus for applying stimulation to a body, the main device comprising a controller and being suitable for connection to one or more interface devices, each interface device being operable to apply stimulation to the body under the control of the controller of the main device, wherein the instructions are executable to cause the processor to control the operation of the controller of the main device. The instructions are preferably executable to cause the processor to control the operation of the controller of the main device by instructing the main device to transmit a start signal to one or more interface devices, wherein the start signal is operable to cause an interface device to apply stimulation to the body. The instructions are preferably executable to allow a user to design a stimulation program. The instructions are executable to cause the processor to transmit a message to the main device, wherein the message specifies one or more parameters of stimulation to be applied to the body by one or more of the interface devices. The parameters include any one or more of: a total number of pulses in a sequence of pulses; an amplitude of one or more pulses; a time at which one or more pulses are to be generated; a number of times that a sequence of pulses is to be repeated; a temperature; and/or a length of time for which a temperature is to be generated.

Also disclosed herein is a method for configuring an apparatus to apply stimulation to a body, the method comprising: identifying one or more stimulation pads connected to the apparatus; receiving a user selection of a stimulation pad; and activating a visual indicator on the stimulation pad selected by the user. The method preferably further comprises displaying a visual representation of one or more identified stimulation pads. Displaying a visual representation of one or more identified stimulation pads preferably comprises displaying a visual representation of each stimulation pad positioned upon a region of the body to which that pad should be attached. Receiving a user selection of a stimulation pad preferably comprises receiving a user selection of a visual representation of one or more identified stimulation pads. Identifying one or more stimulation pads preferably comprises receiving an inventory of stimulation pads connected to the apparatus. Identifying one or more stimulation pads preferably comprises polling one or more interface cards to which the stimulation pads are connected. The method preferably further comprises generating an inventory of stimulation pads connected to the apparatus based upon the polling.

Also disclosed herein is a processor-readable medium comprising instructions which, when executed, cause the processor to perform a method for configuring an apparatus to apply stimulation to a body as described herein.

Also disclosed herein is an apparatus for applying stimulation to a body, the apparatus comprising: means for identifying one or more stimulation pads connected to the apparatus; means for receiving a user selection of a stimulation pad; and means for activating a visual indicator on the stimulation pad selected by the user. The apparatus preferably comprises means for displaying a visual representation of one or more identified stimulation pads. The means for displaying a visual representation of one or more identified stimulation pads is preferably operable to display a visual representation of each stimulation pad positioned upon a region of the body to which that pad should be attached. The means for receiving a user selection of a stimulation pad is preferably operable to receive a user selection of a visual representation of one or more identified stimulation pads. The means for identifying one or more stimulation pads preferably comprises means for receiving an inventory of stimulation pads connected to the apparatus. The means for identifying one or more stimulation pads preferably comprises means for polling one or more interface cards to which the stimulation pads are connected. The apparatus preferably comprises means for generating an inventory of stimulation pads connected to the apparatus based upon the polling.

A further aspect of the invention provides an apparatus substantially as described herein and/or as illustrated in any of the accompanying drawings. A further aspect of the invention provides a method substantially as described herein and/or as illustrated in any of the accompanying drawings.

BRIEF DESCRIPTION OF THE DRAWINGS

Preferred features of the invention will now be described, purely by way of example, with reference to the accompanying drawings, wherein like elements are indicated using like reference signs, and in which.

DETAILED DESCRIPTION

Figure 1:
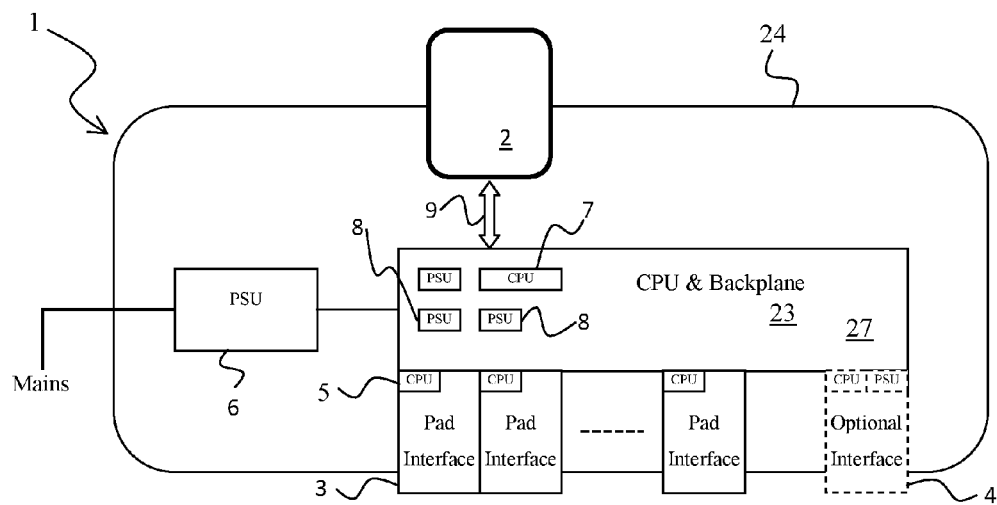
FIG. 1 is a block diagram of a stimulation apparatus according to the invention.
Figure 2:
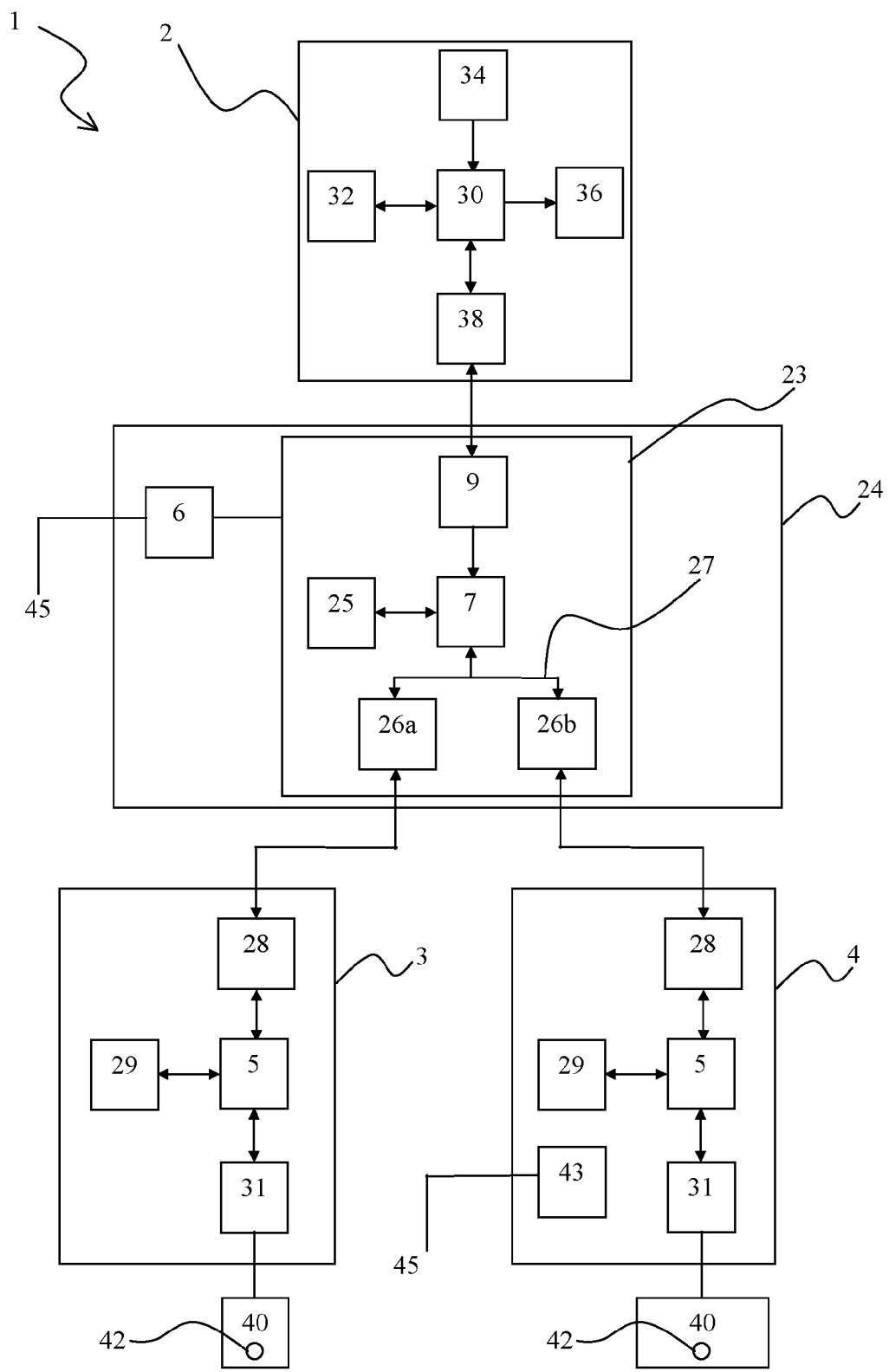
FIG. 2 is a detailed block diagram of the stimulation apparatus illustrated in FIG. 1.

Referring to FIGS. 1 and 2, there is illustrated a stimulation apparatus 1 according to the invention. In a preferred example, the stimulation apparatus 1 is a thermostimulation apparatus that is capable of applying heat therapy and electrical stimulation simultaneously.

The apparatus 1 comprises a main unit 24. The main unit 24 comprises a Central Processing Unit (CPU) 7, a backplane 23, a power supply unit (PSU) 6 and a communication interface 9. The backplane 23 comprises a plurality of electrical connectors 26a, 26b to which a respective interface card 3, 4 can be connected. A preferred example of the backplane 23 comprises twenty such electrical connectors, although other examples of the backplane 23 can comprise more or fewer electrical connectors. The backplane 23 further comprises a bus 27 to enable communication between the CPU 7 and each interface card 3, 4. The bus is preferably an I$^2$C bus, but any other suitable type of bus may be used. The apparatus 1 is preferably powered from a mains electrical supply 45 by means of the PSU 6. The communication interface 9 is operable to enable communication between the CPU 7 and a display and control unit 2. The communication interface 9 may be an Ethernet, IEEE 802.11 (WiFi®), Bluetooth® and/or cellular telephony interface, or any other suitable type of wired or wireless interface.

The apparatus 1 may comprise a display and control unit 2. The display and control unit 2 is preferably a general purpose computer comprising a CPU 30, a memory 32, an input device 34 (such as a touchscreen, keyboard, mouse, touchpad, microphone and/or camera), an output device 36 (such as a display and/or speaker), and a communication interface 38. The memory 32 is suitable for storing instructions that can be executed by the CPU 30 and for storing data. The communication interface of the display and control unit 2 is compatible with the communication interface 9 of the apparatus 1. In a preferred example, the display and control unit 2 is a suitably-programmed Apple® iPad®. However, other types of suitably-programmed computer may also be used, such as a generic tablet, laptop or desktop computer.

The apparatus 1 may also comprise one or more, and preferably up to twenty, thermostimulation interface cards 3 and/or optional interface cards 4. Some embodiments of the invention can have more than twenty thermostimulation interface cards 3 and/or optional interface cards 4. Each interface card 3, 4 has its own CPU 5. Each interface card 3, 4 also comprises a memory 29 suitable for storing instructions that can be executed by the CPU 5 and for storing data. Each interface card 3, 4 further comprises a connector 28 for connection to a corresponding connector 26 of the main unit 24.

Each thermostimulation interface card 3 can be connected to a pad 40 for the application of electric stimulation, heating and/or cooling to a patient. The structure of suitable pads 40 for electric stimulation or thermostimulation is known to those skilled in the art, and need not be described herein. Each thermostimulation interface card 3 may be adapted to receive bio-feedback, such as temperature measurements from thermocouples or temperature sensors located in the pad(s). Suitable temperature sensors include platinum resistance temperature sensors, such as Pt1000 or Pt100 sensors.

Whereas the thermostimulation interface cards 3 are specifically configured to apply electric stimulation, heating and/or cooling, the functionality of the optional interface cards 4 can be much more varied. For example, an optional interface card 4 can be designed to take bio-impedance measurements 16, thereby allowing bio-feedback control by using tissue properties (and, in particular, the impedance of the body) for optimizing the effect of the output from the pad. As another example, other types of optional interface card 4 can be designed to apply ultrasound 17 stimulation, laser 18 stimulation, radio frequency (RF) energy stimulation or microwave energy stimulation, via the use of appropriate transducers in conjunction with the optional interface card 4. For ease of reference, the transducers connected to an optional interface card 4 are referred to herein as pads 40, although it will be appreciated that these pads will have a different structure from those used for thermostimulation if they are designed to apply different stimulation modalities, such as ultrasound or laser stimulation.

The interface cards 3, 4, together with any pads, may be powered from a mains electrical supply 45 via the apparatus 1 by means of the PSU 6. An optional interface card 4 may comprise its own dedicated PSU 43, which may be advantageous if the optional interface card requires a voltage that cannot be provided by PSU 6, or if the stimulation modality provided by the optional interface card consumes more power than can be provided by PSU 6.

Figure 3:
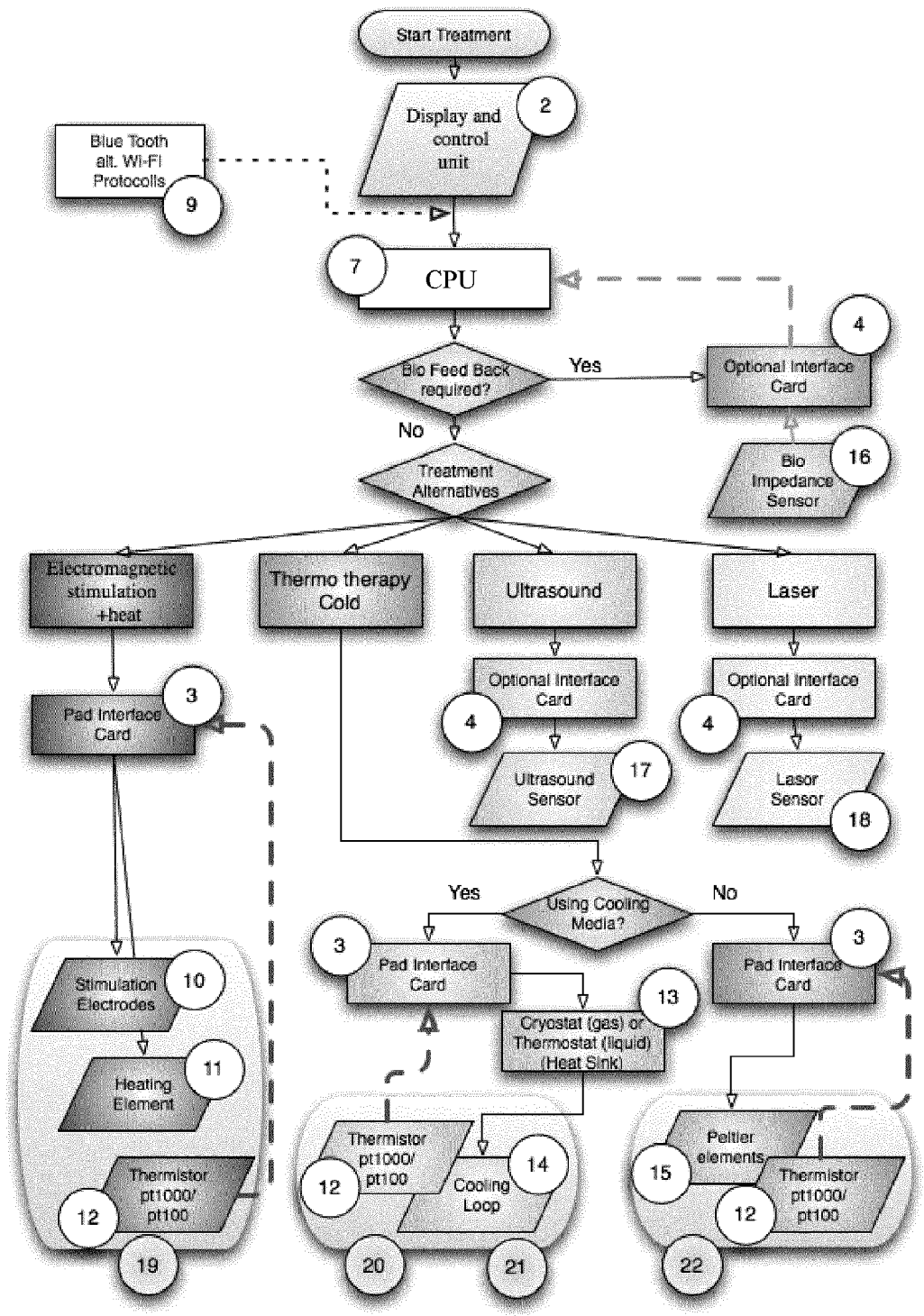
FIG. 3 is a flow chart showing the different parts of the stimulation apparatus according to the invention.

FIG. 3 shows a flow chart providing an overview of an example of a stimulation apparatus as described herein. Three types of pads are illustrated, namely a combined electromagnetic muscle stimulation and heating pad 19, a cooling pad using either cryogenic technology 20 or liquid in combination with a heat sink 21, a combined cooling and heating pad using Peltier elements 22.

The operation and functionality of the stimulation apparatus 1 will now be described.

The display and control unit 2 provides a user interface to the stimulation apparatus 1. For example, the display and control unit 2 allows a user to start, stop, pause and configure the stimulation that is provided by the apparatus 1. The display and control unit 2 is preferably operable to allow a user to design a stimulation program, as described in more detail below. The display and control unit 2 is preferably operable to assist a user in correctly positioning pads on the body, as described in more detail below.

The display and control unit 2 is preferably capable of obtaining software or firmware to be executed by the CPU 7 of the main unit 24 and/or the CPUs 5 of the interface cards 3, 4, and providing that software or firmware to the appropriate CPU 7, 5. In particular, the display and control unit 2 can obtain updated software or firmware having improved functionality, and can provide the updated software or firmware to the appropriate CPU 7, 5 via the communication interfaces 9, 38. The updated software or firmware can be downloaded from a server, via a communication network and communication interface 38, in any suitable manner known to those skilled in the art. In the event that the updated software or firmware is for an interface card 3, 4, the updated software or firmware is received by the CPU 7 of the main unit 24, and then transmitted to the appropriate interface card(s) 3, 4 via the bus 27.

The display and control unit 2 can also store data on a user and his/her treatment program, or can communicate with a remote database via communication interface 38 to store, retrieve and update such user-related data. The display and control unit 2 is preferably operable to play audiovisual media whilst stimulation is in progress, such as advertisements or relaxing music and/or video.

The CPU 7 of the main unit 24 is operable to receive and interpret messages from the display and control unit 2 via the communication interface 9. Several types of messages are provided, each having different functionality as described in the following paragraphs.

A first type of message specifies parameters of electrical stimulation that is to be applied to a patient via a thermostimulation interface card 3. Such a message comprises data fields including: an identifier (such as an address) that uniquely identifies the particular thermostimulation card 3 that is to apply the electrical stimulation; the total number of pulses in a sequence of pulses that is to be applied to a patient; the amplitude (e.g. the voltage) of each pulse in the sequence; the time at which each pulse in the sequence is to be generated; and the number of times that the sequence of pulses is to be repeated.

A second type of message specifies parameters of heat therapy that is to be applied to a patient via a thermostimulation interface card 3. Such a message comprises data fields including: an identifier (such as an address) that uniquely identifies the particular thermostimulation card 3 that is to apply the heat therapy; the temperature that is to be applied to the patient; and the length of time for which that temperature is to be applied.

The parameters of thermostimulation can be specified by a sequence of messages comprising messages of the first and second types, or by a third type of message that specifies the parameters of both electrical stimulation and heat therapy.

A fourth type of message contains data that specifies parameters of stimulation that is to be applied to a patient via an optional interface card 4. The structure of the fourth type of message will depend upon the modality of stimulation that a particular optional interface card 4 is capable of applying and so, for example, the structure of a message for ultrasound 17 stimulation is different from the structure of a message for laser 18 stimulation.

Generally speaking, the CPU 7 of the main unit 24 is operable to receive a message that specifies one or more parameters of stimulation that is to be applied to a patient via the interface cards 3, 4. Upon receiving such a message from the display and control unit 2, the CPU 7 relays the message, via the bus 27, to the CPU 5 of the interface card 3, 4 that was uniquely identified in the message. Upon receiving a message from the CPU 7, the CPU 5 may store the parameters specified in the message in memory 29. The CPU 5 then waits to receive a start signal from the CPU 7 via the bus 27. Upon receiving the start signal from the CPU 7, the CPU 5 causes the interface card 3, 4 to begin applying the stimulation that is specified by the received message. The CPU 5 will continue to cause stimulation to be applied until a stop signal is received from the CPU 7 via the bus 27. If a stop signal is not received, the CPU 5 will cause the stimulation specified by the message to be repeated. The CPU 7 is operable to transmit start signals and stop signals to the CPUs 5 of appropriate interface cards 3, 4 when instructed to do so by the display and control unit 2.

The stimulation that is to be applied to a user can be precisely controlled using the messages described above. These messages can allow stimulation to be tailored to the requirements of a particular user. Furthermore, the efficacy of a particular stimulation regime can be assessed, since precisely controlling the stimulation in this manner can allow a dose-response characteristic to be calculated for a stimulation regime. This can allow more efficacious stimulation regimes to be developed.

The CPU 7 of the main unit 24 is also operable to receive messages from the interface cards 3, 4. In particular, a CPU 5 can transmit messages regarding the status of its associated interface card 3, 4 to the CPU 7. These status messages can include, for example: an indication that an interface card 3, 4 and/or its attached pads 40 are operating normally; a notification of a software error in an interface card 3, 4; a notification of a hardware error in an interface card 3, 4 or its attached pad 40; the temperature of a thermostimulation pad 40; and/or an alarm in the event that the temperature, voltage or current of a thermostimulation pad 40 exceeds a predefined threshold. The CPU 7 can act on these messages in a manner that is appropriate to the content of the message, for example by disabling or resetting a malfunctioning interface card 3, 4, or by sending status information to the display and control unit 2.

Each thermostimulation interface card 3 is operable to drive the currents and voltages needed to provide the desired electrical pulses at a stimulation pad 40, under the control of its CPU 5. The CPU 5 also monitors the actual currents and voltages that are generated. The CPU 5 is able to limit the current and voltage if they are found to exceed predetermined thresholds, thereby ensuring user safety. The CPU 5 may also transmit an alarm message to the CPU 7 of the main device 24 if the current and/or voltage are found to exceed a predetermined threshold.

Each thermostimulation interface card 3 is also operable to generate the current needed for heating a thermostimulation pad during heat therapy, under the control of its CPU 5. It is extremely important that each thermostimulation interface card 3 is electrically isolated so as to prevent the heating current being driven between pads, which might result in a dangerous situation whereby current is driven through the body. In order to prevent a dangerously high current being driven through the body, each thermostimulation interface card 3 contains a circuit for limiting the heating current to a hardwired pre-set maximum value.

As explained above, the apparatus 1 has a distributed control system comprising a first CPU 7 in the main unit 24, a second CPU 30 in the display and control unit 2 and a further CPU 5 in each interface card 3, 4. The second CPU 30 is configured to control the operation of the first CPU 7, whilst the first CPU 7 is configured to control and coordinate the operation of the CPUs 5 in each interface card 3, 4. One advantage of the distributed control system is that it allows the apparatus 1 to stimulate a large number of regions of the body simultaneously, via the addition of extra interface cards 3, 4 and stimulation pads, which can reduce the time taken for treatment if several regions of the body are to be stimulated. This is because each interface card 3, 4 operates under the control of its own CPU 5, which allows the apparatus to be expanded to include a large number of additional interface cards 3, 4 without incurring significant overhead at the other CPUs 7, 30 and without anything more than minor software configuration changes at the other CPUs 7, 30. Similarly, the apparatus 1 can be expanded to allow a stimulation modality that was not envisaged when the apparatus was manufactured, simply by adding an optional interface card 4 that is configured to produce that modality and by reconfiguring the software on the first CPU 7 and second CPU 30.

Another advantage of the distributed control system is that it allows precise control over the time at which each pad 40 generates stimulation. In particular, the distributed control system allows the times at which each pad 40 generates an electric pulse to be coordinated (i.e. such that each pad 40 generates a pulse at a particular time with respect to the pulse generated by each other pad) or synchronised (i.e. such that all pads 40 generate a pulse at the same time). This is because each interface card 3, 4 operates under the control of its own CPU 5, such that the CPU 7 of the main unit 24 is not burdened with generating pulses for several pads at precise moments in time. The CPU 7 of the main unit 24 merely needs to send a start signal to each interface card 3, 4 (or to several interface cards 3, 4) at the correct time, and then each interface card 3, 4 is responsible for generating pulses at the required times. This can advantageously be used to simulate a massaging effect upon a user, by causing each of a plurality of pads 40 to generate pulses at a respective time delay with respect to the pulses generated by other pads of that plurality of pads.

As mentioned above, upon receiving a start signal from the CPU 7, each interface card 3, 4 begins applying the stimulation that is specified by the received message and will repeat that stimulation until a stop signal is received. This will cause the stimulation applied by the interface cards to become desynchronised if two or more interface cards are instructed to apply stimulation programs of different durations. The display and control unit 2 can optionally prevent such desynchronisation by modifying each stimulation program before it is transmitted from the display and control unit 2 to the interface cards 3, 4 via the main unit 24, such that the stimulation programs for each interface card 3, 4 have an equal duration. This is preferably achieved by appending delays (e.g. periods of time where no stimulation occurs) to the shorter stimulation programs, until each stimulation program has the same duration.

The display and control unit 2 preferably comprises a computer program that is operable to allow a user to design a stimulation program. The term 'stimulation program' used herein is preferably understood to mean data and/or one or more instructions that define the parameters of the stimulation that is to be applied by the stimulation apparatus 1 (and, more particularly, by the interface cards 3, 4 thereof). For example, a stimulation program can define the times at which one or more interface cards should apply stimulation, together with any other parameters of the stimulation (e.g. the amplitude of electric pulses, or temperature etc.) for each of the interface cards 3, 4. The computer program allows a user to design a stimulation program by providing a user-friendly way for a user to supply values for any of the parameters of the first, second, third and/or fourth types of message described above. For example, the computer program may be operable to display a graphical user interface through which a user can supply values for the parameters. The computer program is further operable to convert the parameter values supplied by a user into one or more messages, and to transmit those messages to the CPU 7 of the main unit 24 via the communication interfaces 9, 38. The computer program is further operable to store such user-defined stimulation programs in the memory 32 of the display and control unit 2 (and, preferably, in non-volatile memory in the display and control unit 2), or to transmit the user-defined stimulation programs to a remote database or website. The computer program can also retrieve predefined stimulation programs in which the values of the parameters are preset, to convert those parameters' values into one or more messages, and to transmit those messages to the CPU 7 of the main unit 24 via the communication interfaces 9, 38. The predefined stimulation programs can be retrieved from non-volatile memory of the display and control unit 2, or from a remote database or web site.

The modular design of the stimulation apparatus 1, with its ability to have up to twenty interface cards 3, 4 (or even more in some embodiments), allows a large number of stimulation pads to be simultaneously attached to a body. However, some users may experience difficulties in remembering the correct region of the body to which each stimulation pad should be attached. These difficulties may be exacerbated when different stimulation programs and/or different types of stimulation pad are to be applied to different regions of the body, since, in these situations, each pad must be placed on the correct region of the body to ensure optimum stimulation. The display and control 2 unit addresses these difficulties by assisting a user to correctly position the pads.

Figure 4:
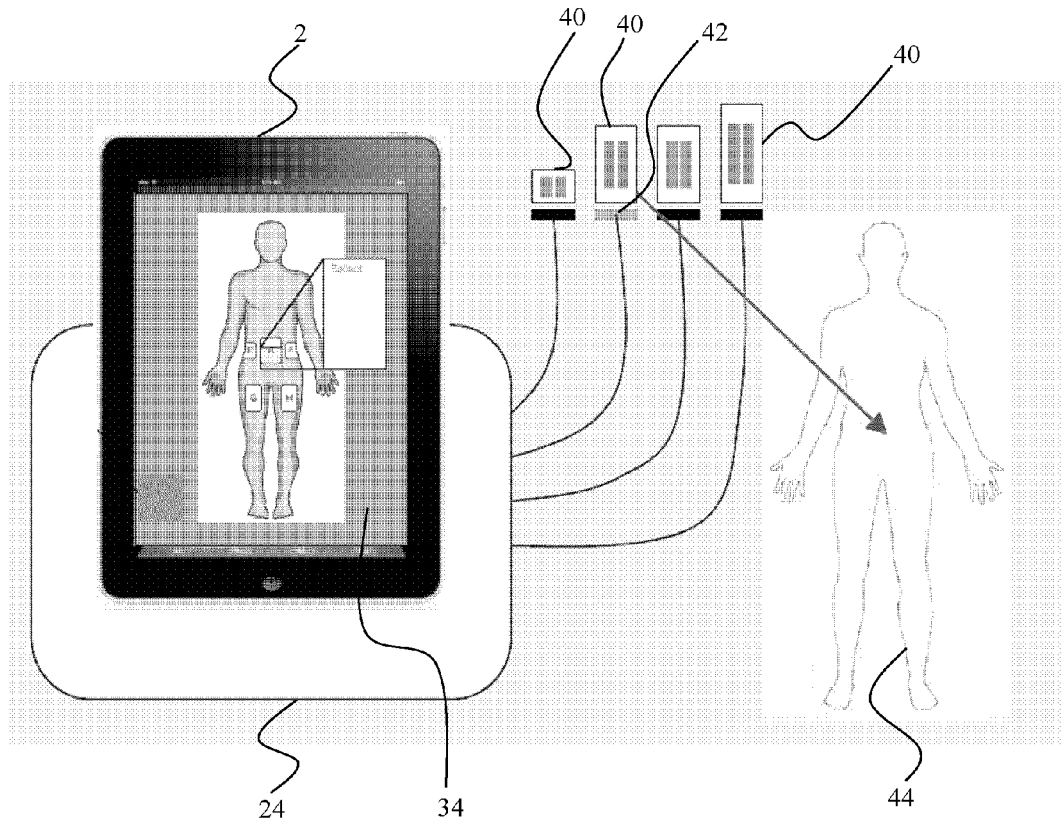
FIG. 4 illustrates the use of the display and control unit to assist a user in placing stimulation pads.

A method 50 performed by the display and control unit 2 to assist a user in correctly positioning stimulation pads 40 on a body will now be described with reference to FIGS. 4 and 5.

The method is preferably performed by executing a suitable computer program on the CPU 30 of the display and control unit 2. The body 44 may be the user's own body or the body of another person or animal. Before the pads 40 are positioned on the body 44, the pads are connected to the main unit 24, via the interface cards 3, 4, by a user.

In step 52, the display and control unit 2 identifies one or more pads 40 that are connected to the main unit 24. Identifying the connected pads preferably comprises determining how many pads 40 are connected to the main unit 24 and determining the properties of each connected pad 40. In this context, the properties of a pad 40 may include the surface area of a pad, its power consumption and/or the stimulation modalities that it is capable of delivering (e.g. whether it is capable of delivering heating and/or cooling, or whether it is capable of delivering electrical, ultrasound, radio-frequency or laser stimulation). In one embodiment, the display and control unit 2 sends a message to the main unit 24, via the communication interfaces 9, 38, to instruct the main unit 24 to provide details of the connected pads 40. Upon receiving the message, the main unit 24 determines which pads 40 are connected by polling each interface card 3, 4. Each interface card 3, 4 then determines whether a pad 40 is connected to it and, if so, determines the properties of the connected pad 40. For example, an interface card 3, 4 can determine the properties of a connected pad 40 by measuring the impedance of the pad 40, or by interrogating logic (such as a microprocessor or memory) integrated in the pad 40 to obtain information regarding the pad's properties. Each interface card 3, 4 responds to the polling by informing the main unit 24, via the bus 27, whether a pad 40 is connected to it and, if so, the properties of the connected pad 40. The main unit 24 then generates an inventory of all connected pads 40, and transmits the inventory to the display and control unit 2 via the communication interfaces 9, 38. The inventory includes data specifying the properties of each connected pad 40 and an identification of the interface card 3, 4 to which each pad 40 is connected. The display and control unit 2 may compare the inventory with the stimulation program that is to be applied, and determine the region of the body to which each pad 40 should be connected in order deliver the stimulation program. The determination of the region of the body to which each pad should be connected is preferably based upon the data specifying the properties of each pad 40 that is contained in the inventory.

In step 54, the output device 36 of the display and control unit 2 displays a visual representation of some or all of the pads 40 that are connected to the main unit 24. Preferably, the output device shows a visual representation of each pad 40 positioned upon the region of the body 44 to which the user should attach that pad 40.

In step 56, the input device 34 of the display and control unit 2 receives a user selection of a particular pad 40. If the input device 34 is a touchscreen, the user can select a particular pad by touching a visual representation of that pad 40. If the input device 34 is a keyboard, the user can select a particular pad 40 by pressing a key that is associated with that pad. It will be appreciated that the user selection of a pad 40 may be received in any other way that is appropriate to the capabilities of the input device 34.

In step 58, the display and control unit 2 causes a visual indicator 42 on the pad 40 selected by a user to be activated. For example, each pad 40 may comprise a light emitting diode (LED), such that the display and control unit 2 causes the LED to be illuminated when a user selects that pad. The display and control unit 2 can cause the visual indicator 42 to be activated by transmitting a message to the main unit 24 via the communication interfaces 9, 38, wherein the message instructs the main unit to activate the visual indicator 42. Upon receiving such a message, the main unit 24 can instruct the interface card 3, 4 to which the pad 40 is attached to activate the visual indicator 42, via the bus 27. Activation of the visual indicator 42 can assist the user in identifying which of the pads 40 corresponds to the pad that the user selected with the input device 34 and, therefore, can assist the user in attaching the correct pad 40 to the correct region of the body 44. Steps 56 and 58 can be repeated until the user has correctly attached all of the pads 40 to the body 44.

Figure 5:
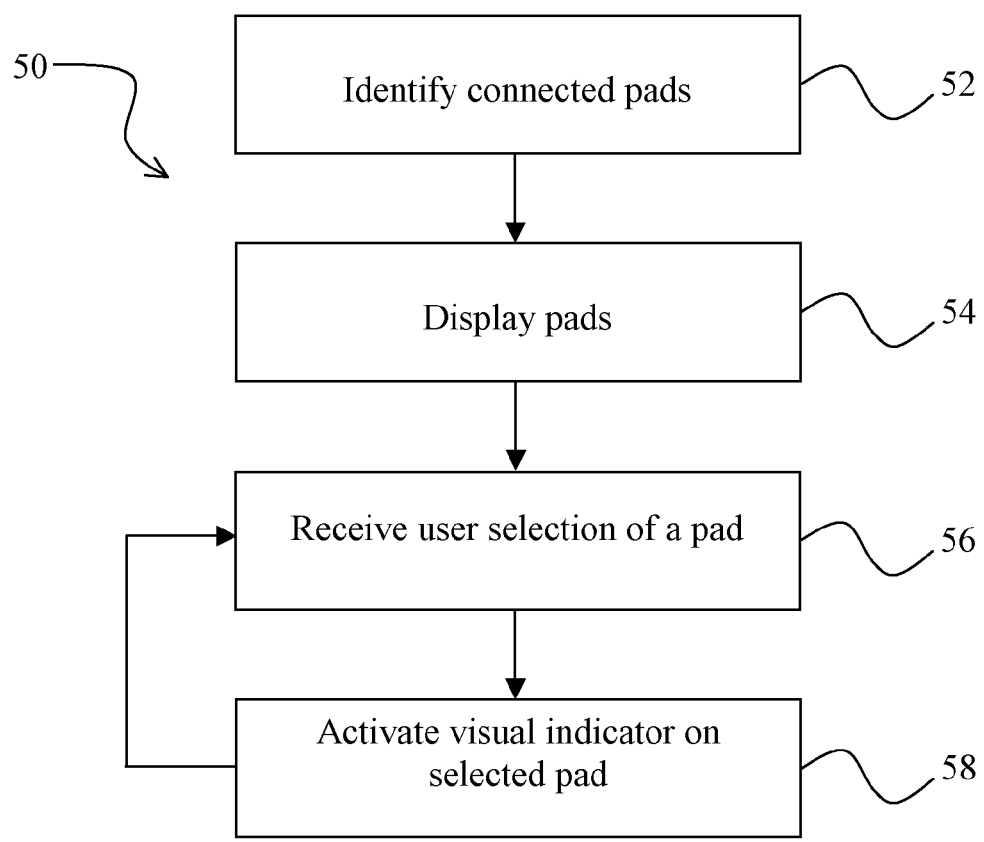
FIG. 5 is a flow chart of a method performed by the display and control unit of the stimulation apparatus to assist a user in placing a stimulation pad.
Figure 6:
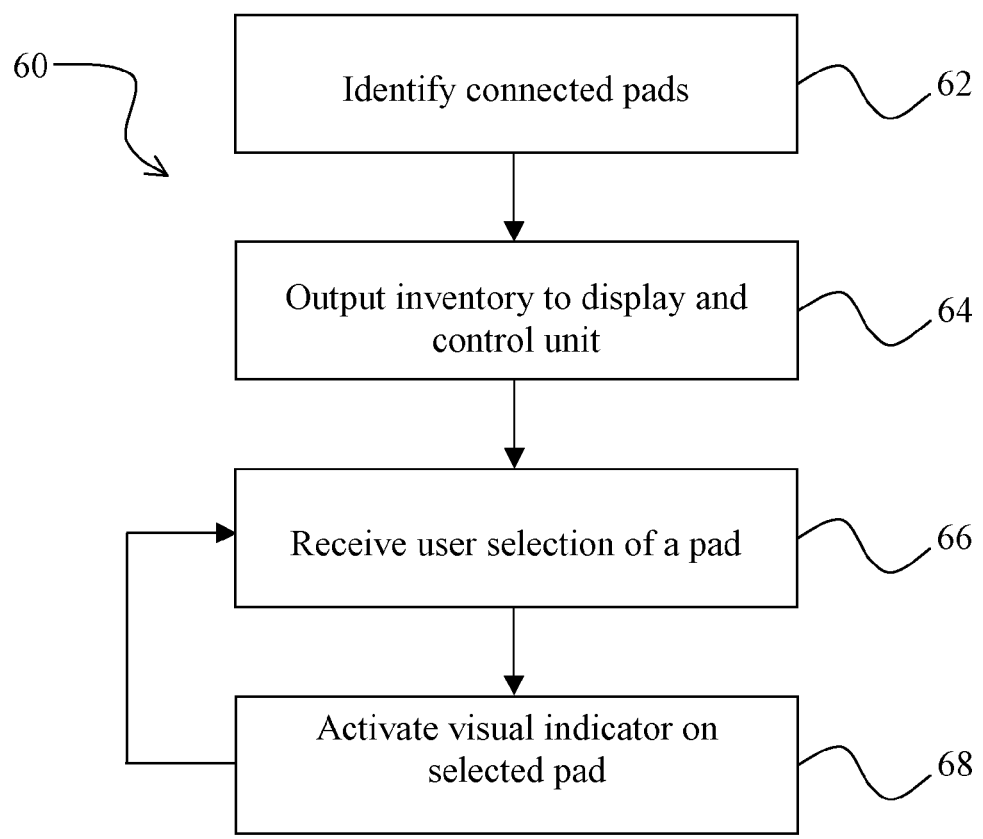
FIG. 6 is a flow chart of a method performed by the main unit of the stimulation apparatus to assist a user in placing a stimulation pad.

FIG. 6 shows the method 60 performed by the main unit 24 whilst the display and control unit 2 is performing the method 50 shown in FIG. 5. In step 62, the main unit 24 identifies one or more pads 40 that are connected by polling each interface card 3, 4, in the method already described in connection with step 52 of FIG. 5. In step 64, the main unit 24 transmits an inventory of all connected pads 40 to the display and control unit 2 via the communication interfaces 9, 38. The inventory includes data specifying the properties of each connected pad 40 and an identification of the interface card 3, 4 to which each pad is connected. In step 66, the main unit 24 receives an instruction from the display and control unit 2, via the communication interfaces 9, 38, to activate the visual indicator 42 of a particular pad 40. Upon receiving the instruction, in step 68 the main unit instructs the interface card 3, 4 to which the pad 40 is attached to illuminate the visual indicator 42. Steps 66 and 68 can be repeated until a user has correctly attached all of the pads 40 to the body 44.

The operation of the CPUs 5, 7, 30 can be controlled by instructions stored on a processor-readable medium. The processor-readable medium may be: a read-only memory (including a PROM, EPROM or EEPROM); random access memory; a flash memory; an electrical, electromagnetic or optical signal; a magnetic, optical or magneto-optical storage medium; one or more registers of a processor; or any other type of processor-readable medium.

The thermostimulation apparatus described herein is particularly advantageous for the treatment of muscular injuries, rehabilitation, but also relaxation and massaging.

It will be understood that the invention has been described above purely by way of example, and that modifications of detail can be made within the scope of the invention.

The invention claimed is:

1. An apparatus for applying stimulation to a body, the apparatus comprising:
   a main device; and
   a plurality of interface devices connected to the main device, each interface device being operable to apply stimulation to the body and comprising a programmable controller for controlling application of stimulation to the body,
   wherein the main device comprises a controller that is operable to transmit a start signal to each controller of the plurality of interface devices,
   wherein the controller of each interface device is operable to cause the respective interface device to begin applying stimulation to the body when the start signal is received, thereby coordinating and/or synchronising a time at which the plurality of interface devices stimulate the body.

2. The apparatus of claim 1, wherein the controller of the main device is operable to control an operation of the controller of each interface device by transmitting a respective message to the controller of an interface device, wherein the message specifies one or more parameters of stimulation to be applied to the body.

3. The apparatus of claim 1, wherein the main device is operable to communicate with a display device, and wherein the controller of the main device is operable to be controlled by the display device.

4. The apparatus of claim 3, wherein the controller of the main device is operable to receive a message from the display device, wherein the message specifies one or more parameters of stimulation to be applied to the body by one or more of the interface devices.

5. The apparatus of claim 1, wherein the controller of an interface device is operable to cause that interface device to apply stimulation to the body in accordance with one or more parameters specified in a message received from the controller of the main device.

6. The apparatus of claim 1, the apparatus further comprising:
a display device operable to communicate with the main device, wherein the display device comprises a controller that is programmed to control an operation of the controller of the main device by instructing the main device to transmit the start signal to the plurality of interface devices.

7. The apparatus of claim 6, wherein the display device comprises a computer program for allowing a user to design a stimulation program.

8. The apparatus of claim 6, wherein the controller of the display device is operable to transmit a message to the main device, wherein the message specifies one or more parameters of stimulation to be applied to the body by one or more of the interface devices.

9. The apparatus of claim 2, wherein the parameters include any one or more of:
a total number of pulses in a sequence of pulses;
an amplitude of one or more pulses;
a time at which one or more pulses are to be generated;
a number of times that a sequence of pulses is to be repeated;
a temperature; and/or
a length of time for which a temperature is to be generated.

10. The apparatus of claim 2, wherein the parameters include any one or more of:
a total number of pulses in a sequence of pulses;
an amplitude of one or more pulses;
a time at which one or more pulses are to be generated;
a number of times that a sequence of pulses is to be repeated;
a temperature; and
a length of time for which a temperature is to be generated.

11. The apparatus of claim 5, wherein the parameters include any one or more of:
a total number of pulses in a sequence of pulses;
an amplitude of one or more pulses;
a time at which one or more pulses are to be generated;
a number of times that a sequence of pulses is to be repeated;
a temperature; and
a length of time for which a temperature is to be generated.

12. A non-transitory processor-readable medium comprising instructions for execution by a processor of a main device for applying stimulation to a body, said main device being simultaneously connected to a plurality of interface devices, each interface device being operable to apply stimulation to the body and comprising a programmable controller for controlling application of stimulation to the body, wherein the instructions are executable to cause the processor to control an operation of the controller of each interface device by transmitting a start signal to each controller of the plurality of interface devices, wherein the controller of each interface device is operable to cause the respective interface device to begin applying stimulation to the body when the start signal is received, thereby coordinating and/or synchronising a time at which the plurality of interface devices stimulate the body.

13. The non-transitory processor-readable medium of claim 12, wherein the instructions are executable to cause the processor to control the operation of the controller of each interface device by transmitting a respective message to the controller of an interface device, wherein the message specifies one or more parameters of stimulation to be applied to the body.

14. The non-transitory processor-readable medium of claim 12, wherein the instructions are executable to cause the processor to receive instructions and/or data from a display device, and to cause the processor to operate in accordance with the instructions and/or data received from the display device.

15. The non-transitory processor-readable medium of claim 14, wherein the instructions are executable to cause the processor to receive a message from the display device, wherein the message specifies one or more parameters of stimulation to be applied to the body by one or more of the interface devices.

16. The non-transitory processor-readable medium of claim 13, wherein the parameters include any one or more of:
a total number of pulses in a sequence of pulses;
an amplitude of one or more pulses;
a time at which one or more pulses are to be generated;
a number of times that a sequence of pulses is to be repeated;
a temperature; and/or
a length of time for which a temperature is to be generated.

* * * * *